United States Patent
Bert et al.

(10) Patent No.: US 8,502,177 B2
(45) Date of Patent: Aug. 6, 2013

(54) IRRADIATION OF AT LEAST TWO TARGET VOLUMES

(75) Inventors: Christoph Bert, Aschaffenburg (DE); Eike Rietzel, Weltersladt (DE)

(73) Assignees: GSI Helmholtzzentrum für Schwerionenforschung GmbH, Darmstadt (DE); Siemens AG, München (DE)

( * ) Notice: Subject to any disclaimer, the term of this patent is extended or adjusted under 35 U.S.C. 154(b) by 89 days.

(21) Appl. No.: 13/125,941

(22) PCT Filed: Oct. 17, 2009

(86) PCT No.: PCT/EP2009/007461
§ 371 (c)(1),
(2), (4) Date: Jun. 16, 2011

(87) PCT Pub. No.: WO2010/049071
PCT Pub. Date: May 6, 2010

(65) Prior Publication Data
US 2011/0272600 A1    Nov. 10, 2011

(30) Foreign Application Priority Data
Oct. 27, 2008 (DE) .......................... 10 2008 053 321

(51) Int. Cl.
*A61N 5/10*    (2006.01)

(52) U.S. Cl.
CPC .................................. *A61N 5/10* (2013.01)
USPC ................. 250/492.3; 250/505.1; 378/65

(58) Field of Classification Search
USPC .................. 250/492.3, 505.1; 378/69, 65
See application file for complete search history.

(56) References Cited

U.S. PATENT DOCUMENTS

| 5,373,844 A * | 12/1994 | Smith et al. .................. 600/427 |
| 6,148,272 A | 11/2000 | Bergstrom et al. |
| 7,027,557 B2 | 4/2006 | Llacer |
| 7,142,635 B2 | 11/2006 | Kamath et al. |

(Continued)

FOREIGN PATENT DOCUMENTS

| DE | 102005034912 | 2/2007 |
| EP | 1378265 | 1/2004 |
| WO | WO 2008116535 | 10/2008 |

OTHER PUBLICATIONS (German Office Action) Deutsches Patent—und Markenamt 80297 Munchen Date: May 12, 2009.

(Continued)

*Primary Examiner* — Kiet T Nguyen
(74) *Attorney, Agent, or Firm* — Reising Ethington PC

(57) ABSTRACT

The invention concerns an idea of planning irradiation of two target points (81, 9) with a beam approaching target points (72) for the purpose of depositing a first target dose distribution in a first of the two target volumes (81, 92) and a second target dose distribution in a second of the two target volumes (81, 92). The idea is characterized by the following steps: assigning target points (72) to one of the target volumes (81, 92), detecting an overlap of a first deposition caused by approaching a target point (72) assigned to the first target volume (81, 92) with a second deposition caused by approaching a target point (72) assigned to the second target volume (81, 92), and adapting the planning process for at least one of the target points (72) whose approach contributes to the overlap of the first and second deposition.

11 Claims, 5 Drawing Sheets

(56) References Cited

U.S. PATENT DOCUMENTS

Figure 1:
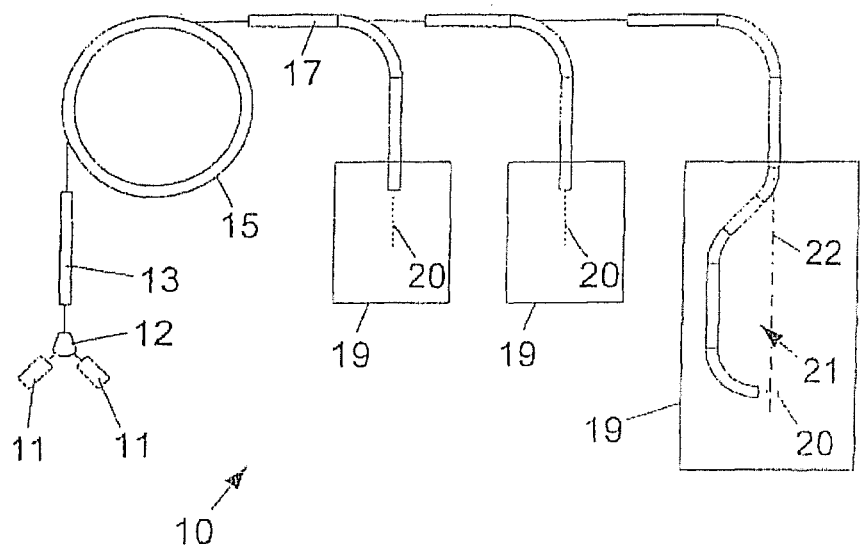

| | | |
|---|---|---|
| 2004/0213381 A1 | 10/2004 | Harada |
| 2004/0254448 A1 | 12/2004 | Amies |
| 2005/0201516 A1 | 9/2005 | Ruchala et al. |
| 2006/0231775 A1 | 10/2006 | Harada |
| 2007/0286343 A1 | 12/2007 | Maciunas |
| 2009/0261275 A1* | 10/2009 | Rietzel ............... 250/492.1 |

OTHER PUBLICATIONS

Pedroni E.etal"The 200-MeV Proton Therapy Project at the Paul Scherrer Institute: Conceptual design & practical realization" 2389MedicalPhysics Jan. 1, 1995 Seiten37-53 XP000505145.

* cited by examiner

- Dividing in several session
- Planning irradiation prior to each session
- Calculating cumulative doses
- Adjusting target volumes
- Providing the target volumes with safety margin
- Changing of irradiation planning because of changes in the target volumes
- Assigning information to individual points

Fig. 6

IRRADIATION OF AT LEAST TWO TARGET VOLUMES

The invention concerns a method for planning irradiation of several target volumes with a beam approaching target points, a method for irradiating such target volumes, a device for irradiating several target volumes, and a control system for controlling such a device.

The irradiation of a target with a beam approaching different target points (beam scanning) is already known. For example, when irradiating tumors, particle beams, especially ion beams, which have in particular protons, a particles or carbon nuclei, are used. The beam sequentially approaches parts of the target region or regions, the target points.

Particle beams are especially advantageous for irradiating target volumes, because toward their end they traverse a maximum of energy deposition (Bragg-Peak). In this way, it is possible to irradiate effectively even imbedded spatial structures without overly damaging the imbedding surroundings. Frequently, spatial target region or regions are irradiated in layers, wherein the beam energy determining the depth of penetration is selected to be constant for each layer (iso-energy layer). Also known is the so-called volumetric scanning (also called "depth scanning") wherein the successively approached target points are not necessarily assigned to individual (iso-energy) layers. Basically, the invention concerns also embodiments in which the beam is formed by means of electromagnetic waves.

Scanning methods allow for irradiation that is adapted to the shape of the target by scanning with a beam. A distinction is made between different scanning methods. Especially grid scanning proved to be effective. In this case, the particle beam remains during a predetermined time period at each of several screen dots to be approached or deposits at each of these screen dots a predetermined number of particles. However, between the screen dots, the particle beam is not, or not always, switched off. However, basically the invention is not restricted to grid scanning but can be used also in connection with spot scanning, a continuous or discontinuous scanning method, or with other scanning methods.

Here, a target volume denotes a spatial region or regions within which a dose is to be deposited that has been predetermined or prescribed by a user, for example, medical staff.

A target point denotes a point which can be defined, for example, by indicating three Cartesian space coordinates (x, y, z) and which is usually located within the object to be irradiated and especially within the target volume.

When using grid scanning, it should be noted that the screen dots can differ from the target points. Usually, target points apply only to a portion of the screen dots, which means that not all screen dots are approached because grids usually do not cover only the target volume(s) but also the surrounding region which is not approached. Furthermore, the screen dots can usually be indicated in the fixed coordinate system, while the target points are possible viewed in the coordinate system of the target. In particular, screen dots and the target points do not have to be mutually congruent.

It is also possible to represent screen dots and target points in a mutual coordinate system. Here, it is useful to drop target points on screen dots.

In a simple case, a target volume and its surrounding region are assigned to a grid covering this volume, wherein the screen dots within the target volume correspond to target points and are assigned to this target volume.

A particle beam involves a beam having a defined cross section consisting of particles and having a defined, usually small spectrum of particle energy. The particle energy represents the energy of an individual particle when entering the object to be irradiated.

When referring to a particle beam directed on a target point, it means that the particle beam (for example, by means of deflection magnets) is directed in x and y direction in such a way that the target point lies in the center or on a line (or its extension) of maximum fluence or dose and that the target point lies in the Bragg-Peak of the particle beam. In particular, this refers to approaching a target point.

When planning irradiation, usually the following parameters are determined for each target point or screen dot: lateral position, energy—determining the depth of penetration, focus and number of particles.

Usually, for example, when irradiating a tumor, the objective is to achieve across the target volume a specific distribution of the dose, a target dose distribution, especially a biologically effective target dose distribution for specific ions. The target dose distribution is quantified as energy deposited per unit volume. Commonly a dose is indicated in joules per kilogram (Gray).

It is generally known to irradiate several target volumes in one session. For example, when irradiating a person, this can involve lung tumors and lymph nodes of the mediastinum. In the process, a similar or a different dose can be applied to the respective target volumes.

The invention is based on the objective of providing an advantageous method for planning irradiation of several target volumes with a beam approaching target points, a respectively advantageous method for irradiating such volumes, a respectively advantageous device for irradiating several target volumes, and an advantageous control system for controlling such a device.

This objective is achieved by a method for planning irradiation of two or more target volumes with a beam approaching target points for the purpose of depositing a dose, deposition for short, a first target dose distribution in a first of two target volumes and a second target dose distribution in a second of two target volumes. The method is characterized by the following steps: assigning target points to one of the target volumes, detecting an overlap of a first deposition caused by approaching a target point assigned to the first target volume with a second deposition caused by approaching a target point assigned to a second target volume, and adapting the planning process for at least one of the target points whose approach contributes to the overlap of the first and second deposition.

Preferred embodiments of the invention are indicated in the dependent claims and are subsequently described in more detail.

A method of "planning irradiation" does not necessarily have to include irradiation itself, but can be performed independent of irradiation. In particular, the planning process can precede irradiation. To simplify matters, the description does not always differentiate this fact. The preceding and following description of individual characteristics of the method refers to the planning method, as well as the irradiation method, without specifically mentioning it in each particular case.

The invention is based on the knowledge that when irradiating several target volumes based on independently planned target dose distributions the possibility of an overlap of depositions can occur. Such overlaps can result in the fact that the actual deposition is locally considerably larger than the respective target dose distribution.

For example, when a first target volume within a body is irradiated according to a first target dose distribution, a certain dose is deposited also along the irradiation entry channel outside of the first target volume. In case a second target volume with an independently determined second target dose distribution is placed in the irradiation entry channel of the first target volume, the entire deposited dose within the second target volume will be larger than after the second target dose distribution.

For example, such an overlap can result also from an overlap of target volumes or from closely positioned target volumes. This can be the case when certain, for example, anatomical structures overlap.

It is also known to provide target volumes with a safety margin that also has to be irradiated which, because of the greater expansion, promotes overlaps. Such safety margins take into consideration encounters of the structures to be irradiated or incorrect positioning. A target volume with a safety margin is also called "planning target volume."

Furthermore, when approaching a target point, the dose is not deposited punctiform but covers also a surrounding region of the target point. Also from this aspect, it is possible that a target point whose nominal position does not lie in an overlap still contributes to an overlap.

Overlaps can especially be generated by moving target volumes. For example, when during the irradiation process of a person a first target volume moves cranially by 1.0 cm and a second adjacent or closely positioned or overlapping target volume moves only by 0.5 cm, this can result in an overlap of depositions or in a change of such an overlap which are usually not compensated by simply adapting the position and/or orientation of the person to be irradiated.

Especially when the target volumes have different target dose distributions, it is not possible to compensate the internal (relative) movement by tracking individual screen dots (see below). For example, during the tracking process, the volumes to be irradiated can be displaced in relation to each other. In this case it is advantageous for the "changed" overlap regions to select the respectively required larger dose. In tracking, this can result in "new" regions which previously did not appear to be overlapping regions.

Furthermore, the invention is based on the experience that irradiation is typically performed in several sessions, for example, in fraction in case of fractioned irradiation, wherein only a fraction of the entire dose to be deposited is deposited in each session. The time interval between fractions usually amounts to one or several days. Therefore, irradiation as a whole usually involves several weeks. Within this time period, the target volumes can change their position, size and shape; which contributes to promoting undesired overlaps.

The invention is based on the idea of assigning the target points to specific target volumes and of determining overlaps of depositions which are caused by approaching target points of differently assigned target volumes. Based on this knowledge, irradiation can be adapted for at least one of the target points whose approach contributes to the overlap.

Consequently, according to the invention, some of the target points, ideally all target points, are respectively assigned to one of the target volumes. In an especially simple case, a first part of the target points is assigned to a first target volume and a second part of the target points is assigned to a second target volume. The invention does not exclude the possibility of assigning individual target points to several target volumes.

The term "assigning" comprises in particular expressions which, to a certain extent, have a more specialized meaning, for example, "classifying", providing with a "label" and "marking."

Preferably, the target points within a target volume are assigned to this particular target volume. When involving an imbedded target volume, it can be reasonable to assign to this volume also points outside of the target volume, however, with a deposition, for example, in the irradiation entry channel. For reasons of simplicity, these points can also be described as target points.

When a grid is available, it is possible that several target points apply to one screen dot. For example, when a first and a second target volume overlap, the screen dots within the overlap can be selected as target point after the first target dose distribution, as well as after the second target dose distribution.

In a representation based on screen dots, we can speak of a "screen dot target dose". This involves the target dose per screen dot which results from adding the target doses of the target points applying to this screen dot. According to the invention, in this case, the screen dot target dose is adapted. Furthermore, this representation involves also the possibility that a screen dot can be assigned to several target volumes, in the sense that the target points applying to this screen dot are respectively assigned to different target volumes.

In an extreme case, it is possible that an overlap results already from approaching a single screen dot, for example, in the case of two target points which are assigned to different target volumes and which apply to the screen dot by approaching the screen dot after a respective first target dose distribution and a respective second target dose distribution.

In order to deposit the entire screen dot target dose, it is not required that the screen dot is approached separately for each target point applying to the screen dot, this can be done in cumulative manner.

The dose actually deposited at different target points is determined (see below) and preferably saved and, for example, filed in a table. Subsequent irradiation can be adapted on the basis on this data, and a pre-dose can be taken into consideration even during irradiation. For more complex cases, it can be required to consider for each irradiated point the dose contribution also at other points, as previously discussed even outside the target volume, wherein one point always involves one volume element, also called voxel.

In this way, it is possible to determine overlaps in the sense described above by comparing the target dose distributions. In particular, it is possible to make adaptations even during irradiation, for example, from one session to the next. When planning irradiation, overlaps can be determined even in the preparation phase by means of simulations.

Ideally, the adaptation should be made in such a way that the actually deposited dose corresponds as closely as possible to the target dose distributions. According to the invention, an "adaptation" corresponds at least to adapting to the intensity of irradiation, for example, by changing the number of particles per deposition or by changing the flow and time of deposition.

If, for example, two target volumes overlap, it is preferred when irradiating tumors that the actually deposited dose in the overlap corresponds to the higher target dose. The adaptation can be made by not approaching some of the target points located in the overlap. This can be described as "inactivation" or "removal from the radiation plan". In this case, it is merely required to inactivate the target points for the lower target dose distribution, and the target points for the higher target dose distribution remain active. Respective screen dots in the overlap are then only approached according to the higher target dose distribution.

In simple cases, such adaptations are restricted to switching target points or screen dots to active or inactive. By means of appropriate combinatorics of screen dots switched active/inactive, it can be endeavored to apply the respectively required dose to the individual target volumes. However, in particular, an adaptation can be made by reducing the dose to be deposited to respective target points/screen dots.

An adaptation in the sense of the invention is not required when no overlap is determined. All target points or screen dots can remain in irradiation planning.

Besides irradiating persons or animals, it is also relevant, for example, in the context of material research, to irradiate organic materials in general, especially cells, or to irradiate even inorganic materials, for example, plastic materials.

On the whole, the invention allows for an independent planning of the target dose distributions for individual target volumes. According to the invention, it is possible to consider possible overlaps, especially overlaps resulting from a movement of the structures to be irradiated, during the irradiation process or even prior to irradiation.

Preferably, the approach of target points is performed in the context of grid scanning. If the target points and the screen dots are described in a mutual coordinate system, the target points apply to at least part of the screen dots. Each individual target volume can be assigned to a separate grid. However, it is also possible to imbed all target volumes in a grid.

In a preferred embodiment of the invention, irradiation is performed in several, at least two, sessions. In this case, the total dose to be applied is distributed to the individual sessions in such a way that the dose corresponds at least as close as possible to the overall target dose distribution.

In principal, irradiation in several sessions is advantageous, especially because it is possible to average errors by means of statistical effects.

As already discussed, it is possible that the structures to be irradiated change their position in relation to each other from one session to the next. It is possible to determine the change in position of the structures (see below) and to track the target volumes respectively (see below). In this way, due to the movement of the structures, overlaps can form from one session to the next. It is especially advantageous when possibly occurring overlaps are determined before each session in order to adapt irradiation in accordance with the invention.

Depending on the structure to be irradiated, relative motions can occur in different time scales. For example, when irradiating a person, the time scale shows motions of fractions of a second (heartbeat), of seconds (breathing), and minutes to days (displacements and changes in shape of anatomical structures, in particular, internal movements).

Even the intervals between sessions can be considerably different. For example, a session of fractioned irradiation can correspond to a session possibly involving several days. However, it is also possible to perform a session per day or several sessions per day. For example, in specific multiple irradiations, the sessions are set to merely several seconds or a few minutes.

The target volume can be determined especially by means of X-ray tomography, ultrasonic diagnostic or sonography, optical coherence tomography, magnetic resonance imaging or nuclear magnetic resonance, computer tomography, positron emission tomography, single photon emission computed tomography (SPECT), electromagnetic impedance tomography (EMIT), neutron tomography or other methods which can be used for three-dimensional or even 2D or 4D imaging of the body or parts of the body to be irradiated. In the process it is possible to determine especially changes in position, size and shape in comparison to the situation on which the original radiation plan was based, or in comparison to the situation of previous sessions.

Preferably, during each session, the dose applied in the respective session is determined or calculated. In this way, the course of irradiation can be well observed.

In particular, it is preferred to calculate the sum of all previously applied doses after each session of irradiation. In the case of deviations, it is thus possible to newly optimize the irradiation plan for further sessions by considering already applied doses.

If required, systematic changes can be recognized in the context of such "subsequent calculation" which makes it possible to react to these changes by adapting irradiation planning.

When there are no changes in the object to be irradiated, the same data records could be used for all sessions. Changes taking place between sessions initiate changes in the data records of the individual sessions. The described change of irradiation planning or the irradiation process can be depicted as adapting to the changes in the object to be irradiated. In the course of repeating the described method prior to selected or all sessions, it is possible to recognize systematic changes which indicate that it would be advantageous to prepare a completely new irradiation plan or to newly optimize an irradiation plan instead of repeatedly adapting the irradiation plan or data record.

When the position and/or shape of at least one of the target volumes changes, the overlap can also change, especially when the change involves the position of the target volumes in relation to each other.

If an irradiation plan already exists, it is preferred to change this plan due to the change in position and/or shape of at least one of the target volumes instead of preparing a new irradiation plan.

In particular, after a change in planning, the change of dose is applied to those target points which otherwise would result in an incorrect dose because of the overlap; possibly this involves merely a small section of all target points. This concerns especially the target points in a safety margin. In the simplest of cases, target points are no longer or even newly approached.

In particular, this can be implemented in that different spatial positions and/or shapes of at least one of the target volumes are considered from the start. For target points located in the safety margin, it is especially possible to calculate different dose contributions depending on the different spatial positions and/or shapes of at least one of the target volumes. This is advantageous because especially in connection with these target points a change in position or shape of at least one of the target volumes frequently results in an incorrect dose. Then, when a change in position or shape actually takes place, it is possible to use the pre-calculated dose contributions for changing an already existing irradiation plan. In this way, it is possible to quickly react to the change in position or shape, and an irradiation plan can be quickly adapted.

As mentioned above, it can also be required to store dose contributions of target points/screen dots even in remote voxels, even outside of the respective target volume.

Advantageously, such dose contributions are already considered in the planning process for each target volume and each respectively associated target point so that it is possible to quickly access the dose contributions in the adaption process from one session to the next, for example, on a daily basis. As a result, it is possible to adapt the desired dose distribution for any volume by means of an appropriate combination especially of screen dots to be approached.

As mentioned above, it is usually reasonable to adjust the target volumes or respective screen dots to the structures to be irradiated. Also here we speak of adaptation, and in this case the term adaptation refers especially to the position of the points. Such adjusting is subsequently described in more detail and is extensively described in DE 10 2006 044 139 A1.

In such an adjusting process, here in the context of irradiating a tumor by using grid scanning, the x and y positions of the screen dots, as well as the energy required for the current anatomy are determined. First of all, the volumes in relation to each other are recorded, and the specific transformation parameters are applied to the screen dot positions in the anatomy, wherein the required energy may have to be newly determined based on the current anatomy. It can also be required to use again interpolation to a regular grid and to adapt the number of particles per screen dot. Transformations can be performed either for the anatomy as a whole or for the individual target volumes.

Preferably, at least one of the target volumes, ideally all target volumes, are respectively provided with a safety margin that also has to be irradiated. In this way, as previously mentioned, irradiation is better protected against errors, for example in positioning the target volume. Especially in this case, overlaps are more likely because the target volumes are respectively enlarged. It is therefore all the more relevant to determine overlaps and a respective adaptation of irradiation.

It is preferred to assign information to the points of the object to be irradiated which exceeds the process of assigning target points to volumes, or which can be even independent of such assignments. For example, for a specific point, information can be provided that energy is deposited by approaching a target volume but the point is not located inside the target volume. For example, this can apply to a point located in the irradiation entry channel. In particular, target points can be provided with further information which exceeds the assignment to a target volume. This can involve the previously deposited dose. The respective data can be filed in a table for further use.

The invention-based objective is also achieved by means of a method for irradiating two target volumes with a beam approaching target points for the purpose of depositing a first target dose distribution in a first of the two target volumes and a second target dose distribution in a second of the two target volumes. The method is characterized by the following steps: assigning target points to one of the target volumes, detecting an overlap of a first deposition caused by approaching a target point assigned to the first target volume with a second deposition caused by approaching a target point assigned to a second target volume, and adapting irradiation for at least one of the target points whose approach contributes to the overlap of the first and second deposition.

Preferably, the method of irradiation comprises the method of planning irradiation described above, especially in one of the preferred embodiments of irradiation planning.

The objective is also achieved by a device for irradiating two or more target volumes with a beam approaching target points for the purpose of depositing a first target dose distribution in a first of the two target volumes and a second target dose distribution in a second of the two target volumes, with an irradiation source and a control system for controlling the device. The device is characterized in that the control system is designed to assign target points to one of the target volumes, to detect an overlap of a first deposition caused by approaching target points assigned to the first target volume with a second deposition caused by approaching target points assigned to a second target volume, and to adapt irradiation for at least one of the target points whose approach contributes to the overlap of the first and second deposition.

Such an irradiation device comprises an irradiation source, especially for generating a particle beam, in particular an ion beam. The irradiation source can consist of an accelerator, especially a synchrotron or cyclotron.

When using an ion beam for irradiation, the irradiation device preferably comprises also a scanning device, or scanner, comprising scanning magnets for deflecting the ion beam. Furthermore, it can preferably comprise an energy modulation system, for example, for "volumetric scanning" and "wobbling."

Preferably, the device for irradiation is designed to perform one of the methods described above; especially in one of the preferred embodiments of the method.

The objective is also achieved by means of a control system for controlling a device for irradiating two target volumes with a beam approaching target points for the purpose of depositing a first target dose distribution in a first of the two target volumes and a second target dose distribution in a second of the two target volumes. The control system is characterized in that it is designed to assign target points to one of the target volumes, to detect an overlap of a first deposition caused by approaching target points assigned to the first target volume with a second deposition caused by approaching target points assigned to a second target volume, and to adapt irradiation for at least one of the target points whose approach contributes to the overlap of the first and second deposition.

In contrast to the irradiation device, the control system does not comprise a radiation source. When the control system is used for controlling an irradiation device for irradiating humans or animals, it is also called a treatment control system (TCS). Preferably, the control system comprises at least one device for detecting the parameters of the irradiation device, for example, the scanner settings and beam properties, and/or it comprises a device for detecting the structures to be irradiated.

The control system can be implemented with the help of a computer or a computer system. For example, such a computer can save information regarding the energy distribution of the sessions and the iso-energy layers, the target points, the screen dots, the target dose per screen dot, the treatment plan or criteria for terminating irradiation. For example, one criterion for terminating irradiation can be that the target dose per target point specified in the treatment plan has been reached. It is useful to file the target dose per target point in a table.

Preferably, the control system is designed for controlling one of the devices for irradiation described above; in particular in one of the preferred embodiments of the irradiation device.

Basically, the invention concerns also a respectively advantageous method for generating a data record, in particular based on the planning method, a method for controlling an irradiation device, in particular based on the irradiation method, and a respectively advantageous computer program product based on the invention.

Preferably, specific dose contributions quantified as particle numbers are combined in a data record which is especially suitable for controlling an irradiation device in a continuous or discontinuous process.

This data record can be used as control data record, which can be used for controlling a device for irradiating while a fraction is applied. In addition, the data record can define the coordinates or x and y positions and the particle energies or the respective z positions of the target points. These coordinates can be respectively adapted on the basis of current data.

It is possible to have a generic dose contribution data record for the individual target points in different depths so that it is not necessary to perform a calculation for each application.

Moreover, it is possible to describe dose contributions of all target points with the generic data record.

The preceding and the following description of the individual characteristics refers to all object involving the process category, as well as the device category, without specifically mentioning it in each particular case. The individual characteristics disclosed in this way can also form a substantial part of the invention in combinations not shown in this context.

The previous and the following description of the individual characteristics refers also to a computer program product with a program code for performing invention-based methods and/or for implementing them on a computer/processor.

Furthermore, the invention can be implemented as a computer program product by means of a program code saved on a machine-readable carrier, for example, a ROM, EPROM, EEPROM, or flash memory, a CD ROM or DVD, or on a disc or hard drive, or in the form of program codes saved as firmware, for performing one of the methods mentioned when the computer program product runs on a computer or processor.

It is also possible to implement the present invention as digital storage medium, for example, ROM, EPROM, EEPROM, or flash memory, CD ROM or DVD or disc or hard drive, with electronically readable control signals, which can interact with a programmable computer or processor system in such a way that one of the methods discussed can be performed.

Subsequently, the invention is described in more detail by means of embodiments.

Figure 2:
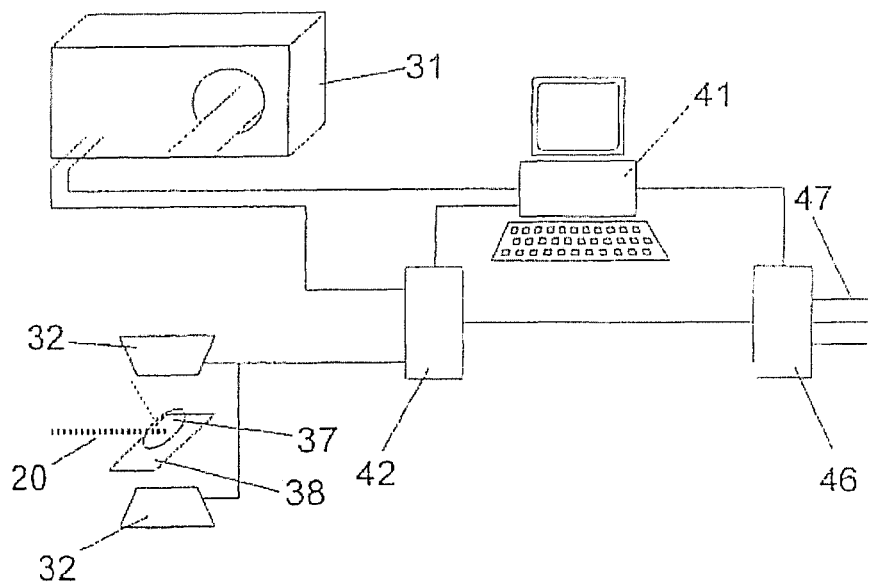
Figure 3:
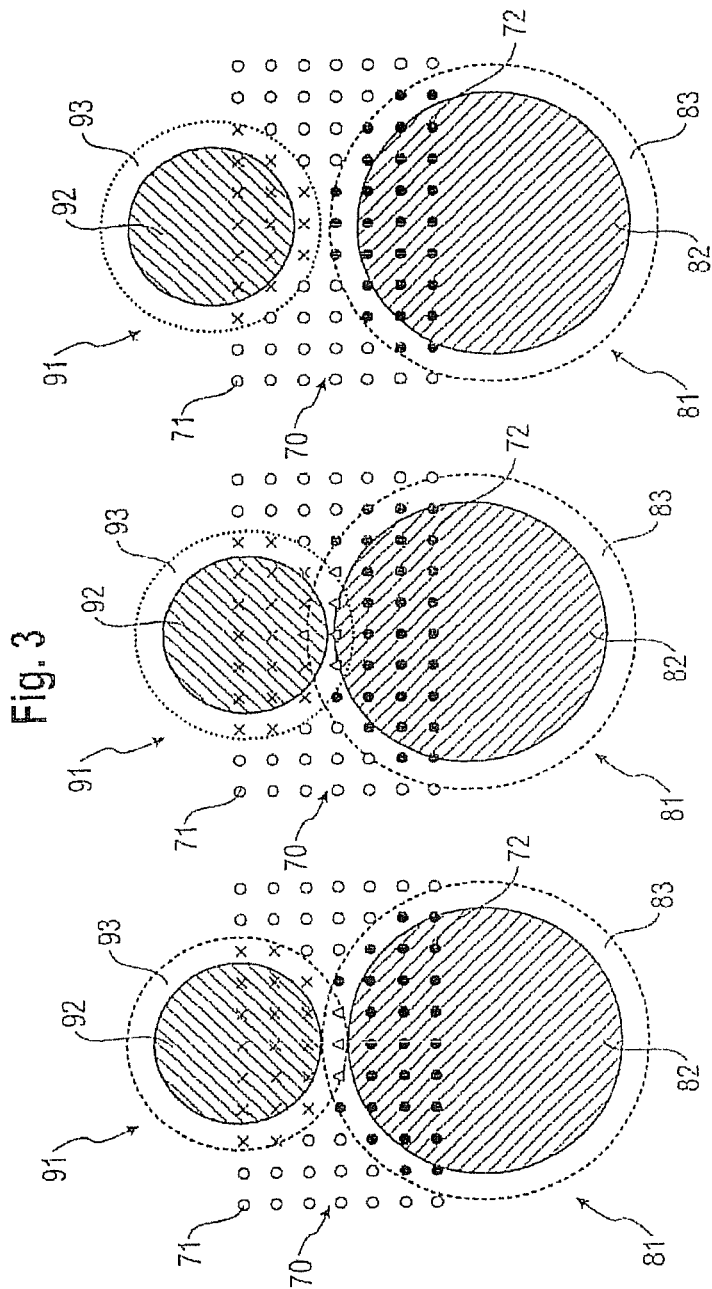
Figure 4:
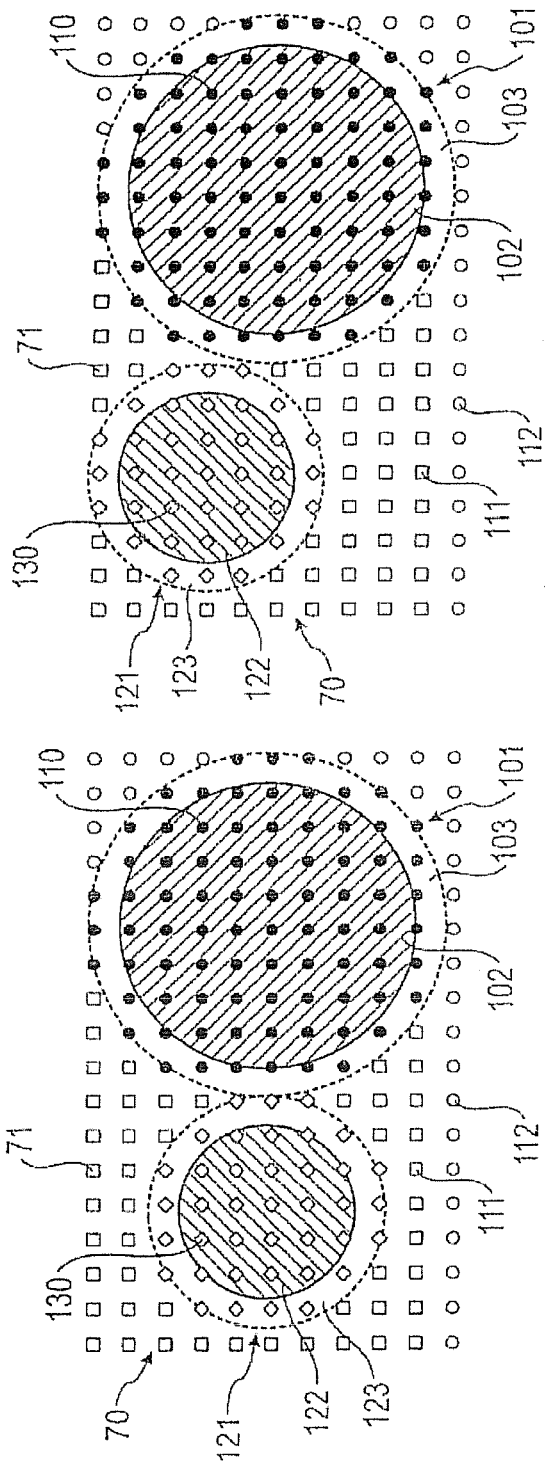
Figure 5:
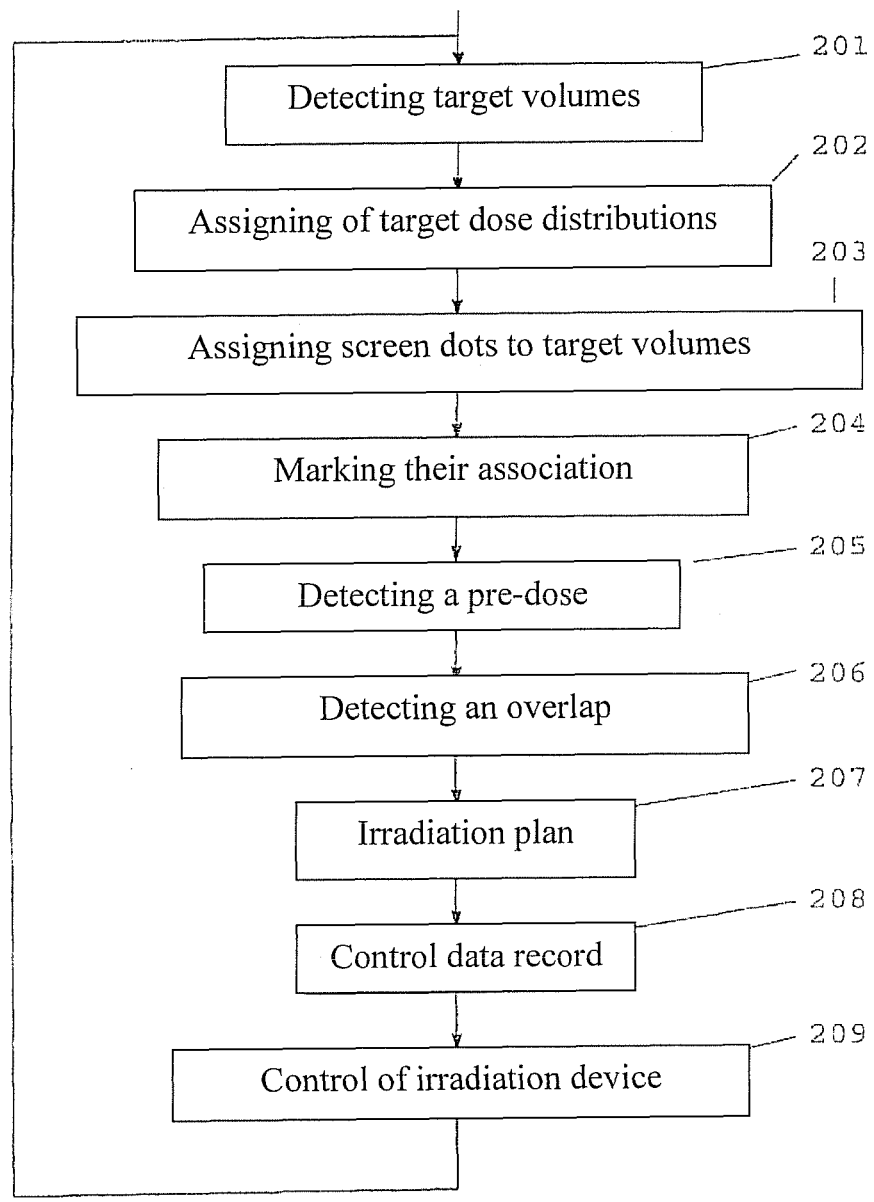

Subsequently, the invention is explained in more detail by means of embodiments and the enclosed figures. It is shown:

FIG. 1 a diagram of an irradiation device;

FIG. 2 a diagram of devices used for irradiation;

FIG. 3 three diagrams of two target volumes cut perpendicular to beam direction;

FIG. 4 two diagrams of two target volumes cut parallel to beam direction;

FIG. 5 a sequence diagram of the method;

FIG. 6 a list of arranging procedural steps.

FIG. 1 shows a schematic overview of the structure of an irradiation system 10 as an example for a system to be used for irradiating a material or body, in particular tumorous tissue in the body, with a particle beam. Particles that can be used include primarily ions, for example, protons, pions, helium ions, carbon ions, neon ions, etc. In principle, the invention can also be implemented with a photon source.

Usually, such particles are generated in a particle source 11. The system 10 shown comprises two particle sources 11 which generate two different types of ion. By means of a switching magnet 12, it is possible to switch between these two types of ion.

The ions are accelerated in the pre-accelerator 13 to a first energy level. For example, the pre-accelerator 13 is a linear accelerator (LINAC). Subsequently, the ions are supplied to an accelerator 15, for example, a synchrotron or cyclotron. In the accelerator 15, they are accelerated to high energies as required for irradiation. After the ions leave the accelerator 15, a high-energy beam transport system 17 guides the particle beam 20 to one or several irradiation chambers 19. In an irradiation chamber 19, the accelerated particles are directed to a body to be irradiated. Depending on the design, this takes place from a fixed direction (in so-called fixed-beam rooms) (see the two on the left of the three rooms 19 shown) or from different directions via a rotatable Gantry 21 that can be swiveled about an axis 22.

FIG. 2 shows a diagram of devices which can be used for an irradiation process according to the invention.

By means of computer tomograph or magnetic resonance tomograph 31 or by means of other diagnostic devices, it is possible to determine position and expansion of a tumor to be irradiated or any other target volume. Data from the tomograph 31 are processed immediately, or after being processed by other devices (not shown in FIG. 2), by means of a device 41 for preparing a data record. For example, the device 41 is a workplace computer, a workstation or a different computer. Furthermore, because of its user interface, software or other characteristics, the device 41 is optionally suitable that the medical staff can define the target volumes, the doses to be applied, the distribution of the doses to several sessions, the direction of irradiation and other details of irradiation.

The irradiation device is controlled with the device 41, as well as with control systems 42, 46 and, if required, also by means of a control line 47. The control systems 42 and 46 comprise devices for determining the status of the irradiation system 10, for example, scanner adjustments and beam characteristics, as well as devices for adjusting the irradiation system 10, for example, a scanner control. The device 41 and the control systems 42 and 46 together correspond to the control system of the irradiation system 10.

The device 10 is able to monitor a body 37 to be irradiated with differently designed control devices before, during or after the irradiation session. For example, a PET camera (PET=positron emission tomography) and/or a computer tomograph (not shown in FIG. 2) are provided to detect a body 37 to be irradiated that is positioned on a hospital bed 38. The PET camera and the hospital bed 38 can be arranged inside one of the irradiation chambers 19 described above by means of FIG. 1. In this case, it is possible to detect in the body 37 to be irradiated the dose generated by the particle beam 20, as well as position, size and shape of the target volumes by means of the PET camera 32 and/or computer tomograph. Alternatively, it is possible to arrange the PET camera 32 and the hospital bed 38 outside an irradiation chamber. Alternatively or additionally, it is possible to prepare a tomography of the body 37 by means of a fluoroscopy device, an X-ray device, an ultrasound sensor and/or other devices that are able to produce three-dimensional images. The imaging method can be performed directly inside the irradiation chamber. However, it can also be performed on the outside—before the patient is brought into the irradiation chamber.

The basic structure of the irradiation system 10 shown in FIG. 1 is typically for several particle therapy systems and other irradiation systems, but the irradiation system can also have a different structure. The subsequently described embodiments can be used in connection with the irradiation system described in FIG. 1 and the systems described in FIG. 2, as well as with other irradiation devices and systems.

FIG. 3 shows a cut perpendicular to the direction of the particle beam inside an iso-energy layer in the context of three different relative spatial arrangements of two target volumes 81 and 91.

Each bottom region shows a hatched planning target volume 81 with an internal region 82 and a safety margin surrounded by a dotted line. Each upper region shows a smaller hatched planning target volume 91 with an internal region 92 and a safety margin surrounded by a dotted line.

In the representation shown on the left, the target volumes 81 and 91 are overlapping. In the representation shown in the center, the overlap is a little larger. And in the representation shown on the right, there is no overlap.

Empty circles in FIG. 3 represent screen dots 71 which are not approached. The screen dots 71 can be arranged in cubical, rectangular, hexagonal or other grids 70. However, screen dots 71 located inside the target volume 81 and 91 are approached. In this example, the positions of the target points 72 overlap with screen dots 71. The target points 72 located inside the target volume 81 are assigned to volume 81. The target points 72 located inside the target volume 91 are assigned to volume 91. Since the target volumes 81 and 91 overlap, a part of the target points is included in the overlap. This results in the situation that these screen dots include a target point assigned to target volume 81, as well as a target point assigned to target volume 91. These positions are represented by empty triangles. The target points exclusively assigned to target volume 81 are represented by filled circles and the target points exclusively assigned to target volume 91 are represented by crosses.

The target dose distributions for the two target volumes 81 and 91 are planned independently from one another. Without an adaptation, the overlap would cause this region to be overdosed.

However, the overlap is detected in the preparation process or during irradiation, for example, between the sessions. According to the invention, it can be adapted.

For example, when a homogeneous target dose A is to be applied to the larger target volume 81 and a homogeneous target dose B to the smaller target volume 91, the screen dots marked with a cross can be approached corresponding to target dose B and the screen dots marked with a filled circle corresponding to target dose A. In this case, dose A would be larger than dose B. It is desired to perform the adaptation in such a way that dose A is also deposited in the overlap. For this purpose, the target points included in the overlap and assigned to the upper target volume 91 are marked as inactive, and the target points included in the overlap and assigned to the upper target volume 81 are marked as active. According to the respectively adapted plan, all screen dots located in the overlap are now respectively approached in order to achieve dose A.

The representation in the center of FIG. 3 shows a case in which the target volumes 81 and 91 have moved closer to each other. Accordingly, the overlap is larger. For example, it can be seen that a screen dot which in the representation on the left is located exclusively in the upper target volume 91 is now included in the overlap (top line within the overlap). Located here is a now inactive target point assigned to the upper target volume 91 and an active target point assigned to the lower target volume. On a whole, dose A is now applied also here.

The representation on the right in FIG. 3 shows a case in which the target volumes 81 and 91 have moved further away from each other. In this case there is no overlap. No intensity adaptation is required. All target points are marked as active. However, from one session to the next, it is examined whether it is possible for an overlap to form.

FIG. 4 shows two cuts in parallel direction of a particle beam coming from the left. In the representation on the left, a larger target volume 101 is shown on the right side. This comprises an internal region 102 and a safety margin 103. Inside the target volume 101 target points 110 are located on a grid 70 with screen dots 71, filled circles which overlap with screen dots 71 and which are assigned to the right target volume 101.

A dose is also deposited in the irradiation entry channel which approaches the right target volume 101 from the left. The respective screen dots 71 are marked with empty squares. These points can also be assigned to the right target volume 101. However, this is not obligatory. It is useful to save regarding these points also the information that they are located outside of the target volume 101. However, these points can also be marked with an index which is different from assigning target points to target volumes and which expresses that these points are associated with the right target volume 101, but they are not located within this target volume 101 or they are not target points of particular this target volume 101. Alternatively, it is also possible to save regarding these target points the information that a dose has been deposited here and that this dose has been generated when irradiating the right target volume 101.

In the irradiation entry channel, a smaller planning target volume 121 is located which has an internal region 122 and a safety margin 123.

Approaching target points 130 located in and assigned to the smaller target volume 121 results in an overlap of the deposition resulting from approaching the target points 110. When the target dose distributions for the target volumes 101 and 121 were planned independently from each other and no adaptation is made, the dose deposited in the left target volume 121 exceeds the desired target dose.

However, here the dose resulting from irradiating the right target volume 10 is considered in connection with the screen dots marked with the rhombuses. The adaptation involves that the target points 130 assigned to the left target volume 121 are approached with a respectively less intensive beam than the target dose that would be required for the target volume 121 alone.

When target volumes are displaced in relation to each other from one session to the next, different dose contributions should be considered when adapting the left target volume 121, see representation on the right in FIG. 4, rhombuses.

The cases represented in FIGS. 3 and 4, i.e., overlap of target volumes and overlap with dose deposited outside of a target volume, are shown separately, for reasons of simplicity. According to the invention, these cases can also be available in combination.

FIG. 5 shows a diagram of a possible course of the process.

In a first step 201, the target volumes according to one of the methods described above are detected. In a second step 202, the target dose distributions are assigned to these target volumes. Already at this point, the positions and target dose distributions can be recorded in a control data record which is later used for controlling the irradiation device, for example, per volume element of the target or per screen dot.

In a third step 203, the screen dots are assigned to the target volumes and in a fourth step 204, their association with one of the target volumes is marked. This marking can also be included in the control data record.

In a fifth step 205, preliminary doses from previous sessions are detected. For example, this takes place by means of a numerical simulation of previous sessions based on then actual situations and measured settings of the irradiation device. Alternatively, the dose applied in each session during irradiation is detected by positron emission tomography using positron emitting nuclides generated during irradiation. Alternatively, it is possible during the process of irradiation, to perform a simulation after each session based on the irradiation parameters measured and to consider the results in the following session.

Furthermore, in a sixth step 206, overlaps are determined.

In a seventh step 207, based on the pre-doses detected and the overlaps determined the irradiation plan is prepared and adapted. In the process, especially the numbers of particles are determined based on the detected current situation, in particular with regard to position, size and shape of the target volumes. Instead of the number of particles, other equivalent parameters can be determined, for example, the total electrostatic charge of particles directed on the target point.

At the latest now, in an eighth step, the control data record is prepared, or else adapted. In a ninth step, this record is used for controlling the irradiation device.

Steps 201 to 209 can be repeated prior to each session. Basically, it is also possible to perform an iteration during a session.

Without overlap all screen dots can remain to be marked as active.

The screen dots belonging to a respective target volume can be adapted by means of a suitable transformation which can be different for different target volumes. In this way, it is also possible to consider different internal movements of the target volumes, which would usually not be possible by merely correcting the position, for example, of a patient.

FIG. 6 shows a list of the arranging procedural steps, comprising:
- dividing irradiation in several sessions so that in each session a part of the target dose is applied, but ultimately the cumulative dose is achieved;
- planning of irradiation prior to each session;
- adjusting the target volumes or respectively adapting the individual screen dots;
- providing the target volumes respectively with a safety margin;
- changing the process of irradiation planning based on a change in shape and/or position of the target volume;
- assigning information to the target points of the body to be irradiated; beyond a mere assignment to the target volume.

In the context of the invention-based adaptive irradiation, especially with particles, with a scanned beam, it is also possible to consider irradiation plans which include several target volumes, especially in the case of adjacent or overlapping target volumes. Without this possibility, safety margins would have to be considered in the case of non-overlapping the target volumes which safety margins include the mobility of all target volumes. This means when a target volume moves along the principal axis of the body and another target volume perpendicular to the principal axis, safety margins have to be considered for both target volumes in both directions when irradiation cannot be adapted individually to the target volumes.

Usually, separate irradiation of the target volumes with respective individual adaptation is not desirable when the target volumes overlap. This results in an overdose in the overlap region when the regions receive individual applications because in both regions the respective prescribed dose is applied. In such cases, the invention is a prerequisite that consistent irradiation can be performed.

The described embodiments are not only suitable to be used in the context of a particle therapy. In addition, they can be generally used in systems for irradiating matter, independent of whether it involves living or dead, organic or inorganic substances, a body of a patient or of an animal to be treated, a phantom, a material sample or a device.

REFERENCE LIST

10 irradiation system
11 particle source
12 switching magnet
13 pre-accelerator
15 accelerator
17 high-energy beam transport system
19 irradiation chamber
20 particle beam
21 Gantry
22 axis of the Gantry 21
31 tomograph
32 PET camera
37 body
38 hospital bed
41 computer
42 control device
46 control device
47 control line
70 grid
71 screen dot
72 target point
81 target volume
82 internal region
83 safety margin
91 target volume
92 internal region
93 safety margin
101 Target volume
102 internal region
103 safety margin
110 target point
121 target volume
122 internal region
123 safety margin
201 first step
202 second step
203 third step
204 fourth step
205 fifth step
206 sixth step
207 seventh step
208 eighth step
209 ninth step

The invention claimed is:

1. Method for planning irradiation of two target volumes (81, 92, 101, 121) with a beam (20) approaching target points (72, 110) for the purpose of depositing a first target dose distribution in a first of the two target volumes (81, 92, 101, 121) and a second target dose distribution in a second of the two target volumes (81, 92, 101, 121), characterized by the following steps:
   - assigning target points (72, 110) to one of the target volumes (81, 92, 101, 121), detecting an overlap of a first deposition caused by approaching a target point (72, 110) assigned to the first target volume (81, 92, 101, 121) with a second deposition caused by approaching a target point (72, 110) assigned to the second target volume (81, 92, 101, 121), and
   - adapting the planning process for at least one of the target points (81, 92, 101, 121) whose approach contributes to the overlap of the first and second deposition.

2. Method according to claim 1, wherein the target points (72, 110) apply to screen dots (71) of a grid (70).

3. Method according to claim 1, wherein the planning process provides irradiation divided in several sessions.

4. Method according to claim 3, wherein irradiation planning is performed prior to each session.

5. Method according to claim 1, wherein a change of one of the target volumes (81, 92, 101, 121) is considered for changing the planning process.

6. Method according to claim 1, wherein planning arranges adjusting the target volumes (81, 92, 101, 121) to structures to be irradiated.

7. Method according to claim 1, wherein each target volume is provided with a safety margin (83, 93, 103, 123).

8. Method according to claim 1, wherein information is assigned to points (72, 110) of an object to be irradiated which exceeds the assignment to a target volume (81, 92, 101, 121).

9. Method for irradiating two target volumes (81, 92, 101, 121) with a beam (20) approaching target points (72, 110) for the purpose of depositing a first target dose distribution in a first of the two target volumes and a second target dose distribution in a second of the two target volumes, characterized by the following steps:

assigning target points (72, 110) to one of the target volumes (81, 92, 101, 121), detecting an overlap of a first deposition caused by approaching a target point (72, 110) assigned to the first target volume (81, 92, 101, 121) with a second deposition caused by approaching a target point (72, 110) assigned to the second target volume (81, 92, 101, 121), and adapting irradiation for at least one of the target points (72, 110) whose approach contributes to the overlap of the first and second deposition.

10. Device (10) for irradiating two target volumes (81, 92, 101, 121) with a beam (20) approaching target points (72, 110) for the purpose of depositing a first target dose distribution in a first of the two target volumes (81, 92, 101, 121) and a second target dose distribution in a second of the two target volumes (81, 92, 101, 121), comprising an irradiation source (11) and a control system (41, 42, 46, 47) for controlling the device (10), characterized in that the control system (41, 42, 46, 47) is designed to assign target points (72, 110) to one of the target volumes (81, 92, 101, 121), detect an overlap of a deposition caused by approaching a target point (72, 110) assigned to the first target volume (81, 92, 101, 121) with a second deposition caused by approaching a target point (72, 110) assigned to the second target volume (81, 92, 101, 121), and to adapt irradiation for at least one of the target points (72, 110) whose approach contributes to the overlap of the first and second depositions.

11. Control system (41, 42, 46, 47) for controlling a device (10) for irradiating two target volumes (81, 92, 101, 121) with a beam (20) approaching target points (72, 110) for the purpose of depositing a first target dose distribution in a first of the two target volumes (81, 92, 101, 121) and a second target dose distribution in a second of the two target volumes (81, 92, 101, 121), characterized in that the control system (41, 42, 46, 47) is designed to assign target points (72, 110) to one of the target volumes (81, 92, 101, 121), to detect an overlap of a first deposition caused by approaching a target point (72, 110) assigned to the first target volume (81, 92, 101, 121) with a second deposition caused by approaching a target point (72, 110) assigned to the second target volume (81, 92, 101, 121), and to adapt irradiation for at least one of the target points (72, 110) whose approach contributes to the overlap of the first and second depositions.

* * * * *